United States Patent
Riether et al.

(10) Patent No.: US 7,928,103 B2
(45) Date of Patent: *Apr. 19, 2011

(54) COMPOUNDS WHICH MODULATE THE CB2 RECEPTOR

(75) Inventors: Doris Riether, Newtown, CT (US); David Smith Thomson, Ridgefield, CT (US); Renee M. Zindell, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/444,919

(22) PCT Filed: Oct. 15, 2007

(86) PCT No.: PCT/US2007/081342
§ 371 (c)(1),
(2), (4) Date: Apr. 9, 2009

(87) PCT Pub. No.: WO2008/048914
PCT Pub. Date: Apr. 24, 2008

(65) Prior Publication Data
US 2010/0029644 A1      Feb. 4, 2010

Related U.S. Application Data

(60) Provisional application No. 60/829,754, filed on Oct. 17, 2006.

(51) Int. Cl.
A61K 31/535    (2006.01)
C07D 413/00    (2006.01)

(52) U.S. Cl. .............. 514/235.5; 514/237.2; 514/239.5; 544/111; 544/141

(58) Field of Classification Search .............. 514/235.5, 514/237.2, 239.5; 544/111, 141
See application file for complete search history.

(56) References Cited

U.S. PATENT DOCUMENTS

| | | | |
|---|---|---|---|
| 3,966,809 A | 6/1976 | Baker et al. | |
| 7,595,397 B2 * | 9/2009 | Zindell et al. | 544/106 |
| 2007/0191340 A1 | 8/2007 | Zindell et al. | |
| 2008/0039464 A1 | 2/2008 | Berry et al. | |
| 2008/0081822 A1 | 4/2008 | Berry et al. | |
| 2009/0275611 A1 | 11/2009 | Riether et al. | |
| 2010/0009964 A1 | 1/2010 | Berry et al. | |
| 2010/0029644 A1 | 2/2010 | Riether et al. | |
| 2010/0076029 A1 | 3/2010 | Bartolozzi et al. | |
| 2010/0081644 A1 | 4/2010 | Bartolozzi et al. | |
| 2010/0261708 A1 | 10/2010 | Cirillo et al. | |

FOREIGN PATENT DOCUMENTS

| | | |
|---|---|---|
| WO | 2004/018433 A1 | 3/2004 |
| WO | 2006/095159 A1 | 9/2006 |
| WO | 2007/070760 A2 | 6/2007 |
| WO | 2007118041 A1 | 10/2007 |
| WO | 2008014199 A2 | 1/2008 |
| WO | 2008039645 A1 | 4/2008 |
| WO | 2008048914 A1 | 4/2008 |
| WO | 2008064054 A2 | 5/2008 |
| WO | 2008098025 A1 | 8/2008 |
| WO | 2009055357 A1 | 4/2009 |
| WO | 2009061652 A1 | 5/2009 |
| WO | 2009105509 A1 | 8/2009 |
| WO | 2009140089 A2 | 11/2009 |
| WO | 2010036630 A2 | 4/2010 |
| WO | 2010036631 A2 | 4/2010 |
| WO | 2010077836 A2 | 7/2010 |
| WO | 2010096371 A2 | 8/2010 |
| WO | 2010147791 A1 | 12/2010 |
| WO | 2010147792 A2 | 12/2010 |

OTHER PUBLICATIONS

Igarashi J and Kobayashi Y, "Improved synthesis of quinine alkaloids with the Teoc protective group," Tetrahedron Letters, Sep. 2005, 46(37), 6381-6384.*
International Search Report for PCT/US2007/081342 mailed Mar. 3, 2008.
Cartwright, D., et al., "Abnormal Nucleophillic substitution in 3-trichloromethylpyridine, its N-oxide and 3,5-Bis(trichloromethyl)pyridine". Tetrahedron, Elsevier Science Publishers, Amsterdam, vol. 51, No. 47, 1995, pp. 12791-12796.
Gartst, M., et al., "Hydroformylation of bisolefinic amine derivatives catalyzed by cobalt and rhodium". Journal of Organic Chemistry, vol. 46, 1981, pp. 4433-4438.
J. Igarashi, et al., "Improved synthesis of quinine alkaloids with the Teoc protective group". Tetrahedron letters, Elsevier, Amsterdam, vol. 46, No. 37, 2005, pp. 6381-6384.
Yordanova, K. et al. "New method for the synthesis of 2,4-disubstituted morpho-lines". Chemical Abstracts, vol. 97, No. 17, Oct. 25, 1982, Columbus, Ohio, USA Chemical Abstracts, vol. 97, No. 17, Oct. 25, 1982, Columbus, Ohio, vol. 115, No. 7, pp. 2635-2642.

* cited by examiner

*Primary Examiner* — San-ming Hui
*Assistant Examiner* — Paul Zarek
(74) *Attorney, Agent, or Firm* — Michael P. Morris; Anthony P. Bottino

(57) ABSTRACT

Compounds of formula (I) are disclosed. Compounds according to the invention are agonists, antagonists or inverse agonists of the CB2 receptor, and are useful for treating inflammation. Those compounds which are agonists are additionally useful for treating pain.

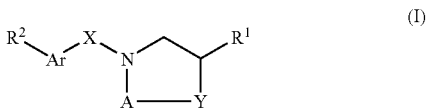

(I)

7 Claims, No Drawings

COMPOUNDS WHICH MODULATE THE CB2 RECEPTOR

APPLICATION DATA

This application is a 371 National Stage filing of PCT/US2007/081342 filed on Oct. 15, 2007. This application also claims benefit to U.S. provisional application Ser. No. 60/829,754 filed on Oct. 17, 2006.

BACKGROUND OF THE INVENTION

1. Technical Field

The present invention relates to novel compounds which modulate the CB2 receptor and their use as medicaments.

2. Background Information

Cannabinoids are a group of about 60 distinct compounds found in *Cannabis sativa* (also know as marijuana) with cannabinol, cannabidiol and $\Delta^9$-tetrahydrocannabinol (THC) being the most representative molecules. The therapeutic usage of *Cannabis* can be dated back to ancient dynasties of China and includes applications for various illnesses ranging from lack of appetite, emesis, cramps, menstrual pain, spasticity to rheumatism. The long history of *Cannabis* use has led to the development of several pharmaceutical drugs. For example, Marinol and Cesamet which are based on THC and its analogous nabilone, respectively, are used as anti-emetic and appetite stimulant. Despite of the clinical benefits, the therapeutic usage of cannabis is limited by its psychoactive effects including hallucination, addiction and dependence. Mechoulam R, ed. *Cannabinoids as Therapeutic Agents*, Boca Raton, Fla.; CRC Press, 1986 provides a review of the medicinal use of cannabis.

The physiological effects of cannabinoids are mediated by at least two G-protein coupled receptors, CB1 and CB2. Autoradiographic studies have demonstrated that CB1 receptors are expressed primarily in the central nervous system, specifically in the cerebral cortex, hippocampus, basal ganglia and cerebellum. They are also found to a lesser degree in the reproductive system and other peripheral tissues including that of the immune system. CB1 receptors regulate the release of neurotransmitters from the pre-synaptic neurons and are believed to mediate most of the euphoric and other central nervous system effects of cannabis, such as THC-induced ring-catalepsy, hypomobility, and hypothermia, which were found to be completely absent in mice with a deletion of the CB1 gene (Zimmer et al., "Increased mortality, hypoactivity, and hypoalgesia in cannabinoid CB1 receptor knockout mice." Proc Natl Acad Sci USA. (1999) 96:5780-5785).

CB2 receptors are almost exclusively found in the immune system, with the greatest density in the spleen. It is estimated that the expression level of CB2 in the immune cells is about 10 to 100 times higher than CB1. Within the immune system, CB2 is found in various cell types, including B cells, NK cells, monocytes, microglial cells, neutrophils, T cells, dentritic cells and mast cells, suggesting that a wide range of immune functions can be regulated through CB2 modulators (Klein et al., The cannabinoid system and immune system. J Leukoc Biol (2003) 74:486-496). This is supported by the finding that the immunomodulatory effect of THC is absent in CB2 deficient mice mice (Bicklet et al., Immunomodulation by cannabinoid is absent in mice deficient for the cannabinoid CB2 receptor. Eur J Pharmacol (2000) 396:141-149). CB2 selective ligands have been developed and tested for their effects in various inflammatory settings. For example, in animal models of inflammation, CB2 selective agonists, inverse agonists and antagonists have been shown to be effective in suppressing inflammation (Hanus et al., HU-308: a specific agonist for CB(2), a peripheral cannabinoid receptor. Proc Natl Acad Sci USA. (1999) 96:14228-14233, Ueda et al., Involvement of cannabinoid CB(2) receptor-mediated response and efficacy of cannabinoid CB(2) receptor inverse agonist, JTE-907, in cutaneous inflammation in mice. Eur J. Pharmacol. (2005) 520:164-171 and Smith et al., The anti-inflammatory activities of cannabinoid receptor ligands in mouse peritonitis models Eur J. Pharmacol. (2001) 432:107-119.). Furthermore, CB2 selective agonists inhibit disease severity and spasticity in animal models for multiple sclerosis (Baker et al., Cannabinoids control spasticity and tremor in a multiple sclerosis model. Nature (2000) 404:84-87. Arevalo-Martin et al., Therapeutic action of cannabinoids in a murine model of multiple sclerosis J. Neurosci. (2003) 23:2511-2516.). Taken together, these results support the notion that CB2 receptor modulators can be employed for the treatment of medical conditions having an inflammatory component.

In addition to inflammation, CB2 agonists have been shown to inhibit pain and emesis. For instance, CB2 selective agonists blunt the pain response induced by thermal or other stimuli (Malan et al., CB2 cannabinoid receptor-mediated peripheral antinociception. Pain. (2001) 93:239-45 and Nackley et al., Selective activation of cannabinoid CB(2) receptors suppresses spinal fos protein expression and pain behavior in a rat model of inflammation. Neuroscience (2003) 119:747-57.) CB2 activation has also been demonstrated to inhibit neuropathic pain response (Ibrahim et al., Activation of CB2 cannabinoid receptors by AM1241 inhibits experimental neuropathic pain: pain inhibition by receptors not present in the CNS. Proc Natl Acad Sci USA. (2003) 100: 10529-33.) Finally, in contrast to the earlier data which did not find CB2 in the brain, a recent article demonstrated the expression of CB2 in the brain, at about 1.5% of the level in the spleen. CB2 activation is shown by this article to be responsible for the anti-emetic effect of endocannabinoid (Van Sickle et al., Identification and functional characterization of brainstem cannabinoid CB2 receptors. Science. 2005 310:329-332.) The foregoing results confirm that CB2 agonists can be used for the treatment of inflammatory and neuropathic pain as well as emesis.

BRIEF SUMMARY OF THE INVENTION

The present invention provides novel compounds which bind to and are agonists, antagonists or inverse agonists of the CB2 receptor. The invention also provides a method and pharmaceutical compositions for treating inflammation by way of the administration of therapeutic amounts of these compounds. Lastly, the invention provides a method and pharmaceutical compositions for treating pain by way of the administration of therapeutic amounts of the new compounds which are CB2 agonists.

DETAILED DESCRIPTION OF THE INVENTION

In its broadest generic aspect the invention provides compounds of the formula

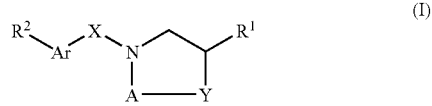

wherein,

R¹ is a hydrogen, $C_1$-$C_6$ alkyl, $C_3$-$C_{10}$ cycloalkyl, aryl optionally substituted with 1-3 substituents, heteroaryl optionally substituted with 1-3 substituents; or, R¹ is $C_1$-$C_3$ alkyl substituted with Z-R⁴, wherein Z is O, S, $SO_2$, NH, NMe or $CH_2$ and R⁴ is aryl or heteroaryl optionally substituted with 1-3 substituents or fused with an aromatic ring;

R² is H, NR⁵R⁶, OR⁶, $SO_2$R⁶, $CH_2$R⁶ wherein R⁵ is hydrogen or $C_1$-$C_6$ alkyl and R⁶ is substituted aryl or heteroaryl optionally substituted with 1-3 substituents;

A is a straight-chain alkanediyl group of n carbon atoms (wherein n is 1, 2 or 3), which is optionally substituted with one or two $C_1$-$C_6$ alkyl groups;

Y is —$(CH_2)_n$—, provided that n is 1 or 2, wherein said methylene group is optionally substituted with a halogen atom or with a $C_1$-$C_6$ alkyl group (which, in turn, is optionally substituted with one to three halogen atoms); or, Y is selected from the group consisting of O and NR³, provided that n is 1 or 2, wherein, R³ is hydrogen, $C_1$-$C_6$ alkyl (optionally substituted by one to 3 halogen atoms), $C_3$-$C_6$ cycloalkyl, phenyl, benzyl, pyridyl, C(O)R⁷, $SO_2$R⁷ or C(O)NHR⁷, C(O)NMeR⁷, wherein, R⁷ is hydrogen, $C_1$-$C_6$ alkyl (optionally substituted by one to 3 halogen atoms), $C_3$-$C_6$ cycloalkyl, phenyl, benzyl or pyridyl; or, Y is selected from the group consisting of S, SO and $SO_2$, provided that n is 2;

X is a methylene group (which is optionally mono- or disubstituted with methyl) or a carbonyl group; and, Ar is a divalent moiety which is either phenylene or a 5-6 membered heteroarylene, which divalent moiety is optionally mono- or disubstituted with moieties selected from the group consisting of $C_1$-$C_6$ alkyl (optionally substituted by 1-3 halogens), $C_3$-$C_{10}$ cycloalkyl and halogen.

In a first subgeneric aspect, the invention provides compounds of the formula I wherein, R¹ is a phenyl;

R² is H, NR⁵R⁶, OR⁶, $SO_2$R⁶ or $CH_2$R⁶, wherein R⁵ is hydrogen and R⁶ is a phenyl, quinolinyl, isoquinolinyl, pyridinyl, pyrimidinyl, or isoxazolyl which is optionally mono- or di-substituted with $C_{1-6}$ alkyl chain, chlorine, fluorine, $C_{1-3}$ alkoxy chain which is optionally substituted with fluorine, or a combination thereof or fused to an aromatic ring such as a naphthyl or quinoline;

A is a straight-chain alkanediyl group of n carbon atoms (wherein n is 1, 2 or 3), Y is —$(CH_2)_n$—, provided that n is 1 or 2, or, Y is O;

X is a methylene group; and,

Ar is a 1,4-phenylene or 1,4-pyridylene.

In a further subgeneric aspect, the invention provides compounds of the formula I wherein, R¹ is a phenyl;

R² is H, NR⁵R⁶, OR⁶, $SO_2$R⁶, $CH_2$R⁶ wherein R⁵ is hydrogen and R⁶ is a phenyl, quinolinyl, isoquinolinyl, pyridinyl, or pyrimidinyl which is optionally mono- or di-substituted with $C_{1-6}$ alkyl chain, chlorine, fluorine, C1-3 alkoxy chain which is optionally substituted with fluorine, or a combination thereof or fused to an aromatic ring such as a naphthyl or quinoline;

A is a straight-chain alkanediyl group of n carbon atoms (wherein n is 2),

Y is O;

X is a methylene group; and,

Ar is a 1,4-phenylene or 1,4-pyridylene.

The invention also includes tautomers, prodrugs and pharmaceutically acceptable salts of the above-described compounds of formula I. In addition, the invention includes amorphous or crystalline forms of the compounds, and isolated isomorphs or polymorphic mixtures, if present.

Compounds of the formula I modulate the activity of the CB2 receptor. By virtue of this fact the compounds of the formula I can be used for treating inflammation, in a manner described more fully below.

Those compounds of the formula I which are agonists of the CB2 receptor can additionally be used for treating pain, in a manner described more fully below.

General Synthetic Methods

The invention also provides processes for making compounds of Formula (I). In all schemes, unless specified otherwise, Ar, $R_1$, $R_2$, A, X, and Y in the formulas below shall have the meaning of Ar, $R_1$, $R_2$, A, X, and Y in Formula (I) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization. The examples which follow are illustrative and, as recognized by one skilled in the art, particular reagents or conditions could be modified as needed for individual compounds without undue experimentation. Starting materials and intermediates used, in the schemes below, are either commercially available or easily prepared from commercially available materials by those skilled in the art.

Compounds of Formula (I) may be synthesized by the methods illustrated in Scheme 1-3

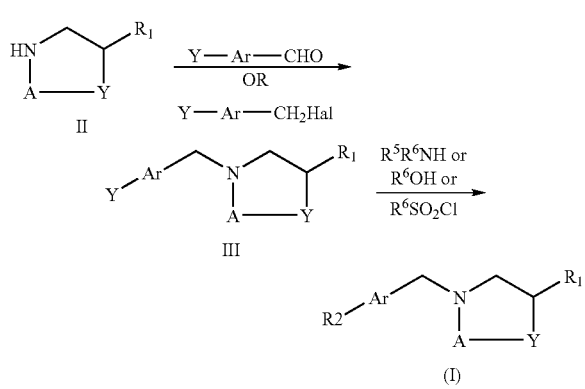

X = $CH_2$

R² = —NR⁵R⁶   or

= —OR⁶   or

= —$SO_2$R⁶

As illustrated in Scheme 1, reacting an amine of formula TI with an aldehyde of formula Y—Ar—CHO (Y is Cl, F, Br, OR⁶, $SO_2$R⁶) or a ketone, in a suitable solvent such as THF, in the presence of a suitable reducing agent provides the alkylated amine of formula III or compound of formula I. Alternatively, the starting amine TI may also be reacted with an halide of formula Y—Ar—$CH_2$-Hal (Hal is Cl, Br or I), in a suitable solvent such as acetonitrile, in the presence of a base such as potassium carbonate to provide the alkylated amine of formula III. The appropriately substituted starting amine TI may be obtained either commercially or made by procedures known to one skilled in the art.

Reacting the intermediate of formula III with an amine of formula $R^5R^6NH$ in the presence of a suitable base with or without palladium catalyst provides a compound of formula (I) where $R^2$ is —$NR^5R^6$. Alternatively, reacting the intermediate of formula III with a phenol of formula $R^6OH$, in a suitable solvent, in the presence of a suitable base, or in the presence of a suitable base and copper iodide provides a compound of formula (I) where $R^2$ is —$OR^6$. The intermediate of formula III may also be reacted with a sulfonyl chloride of formula $R^6SO_2Cl$, in a suitable solvent, in the presence of a suitable base to provide a compound of formula (I) where $R^2$ is —$SO_2R^6$. Alternately, the intermediate of formula III may also be reacted with thiol of formula $R^6SH$, in a suitable solvent, in the presence of a suitable base to provide a thio-ether which may be oxidized to provide a compound of formula (I) where $R^2$ is —$SO_2R^6$. The appropriately substituted starting amine, phenol and sulfonyl chloride may be obtained either commercially or made by procedures known to one skilled in the art.

Further modification of the initial product of formula (I), by methods known in the art and illustrated in the Examples below, may be used to prepare additional compounds of this invention.

Compounds of formula (I), wherein X is a carbonyl may be prepared by the method outlined in Scheme 2

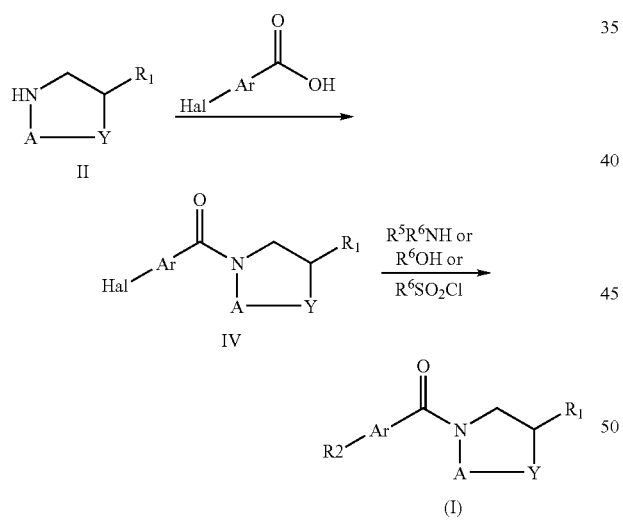

An example of suitable coupling conditions is treatment of a solution of the carboxylic acid in a suitable solvent such as DMF with EDC, HOBT, and a base such as diisopropylethylamine, followed by the desired amine. Alternatively, reaction of the carboxylic acid with reagents such as oxalyl chloride provides the corresponding acid chloride. Reaction of the acid chloride with the desired amine in a suitable solvent provides a compound of formula (IV).

Reacting the intermediate of formula IV with an amine of formula $R^5R^6NH$ in the presence of a suitable base with or without palladium catalyst provides a compound of formula (I) where $R^2$ is —$NR^5R^6$. Alternatively, reacting the intermediate of formula III with a phenol of formula $R^6OH$, in a suitable solvent, in the presence of a suitable base, or in the presence of a suitable base and copper iodide provides a compound of formula (I) where $R^2$ is —$OR^6$. The intermediate of formula III may also be reacted with a sulfonyl chloride of formula $R^6SO_2Cl$, in a suitable solvent, in the presence of a suitable base to provide a compound of formula (I) where $R^2$ is —$SO_2R^6$. Alternately, the intermediate of formula III may also be reacted with thiol of formula $R^6SH$, in a suitable solvent, in the presence of a suitable base to provide a thio-ether which may be oxidized to provide a compound of formula (I) where $R^2$ is —$SO_2R^6$. The appropriately substituted starting amine, phenol and sulfonyl chloride may be obtained either commercially or made by procedures known to one skilled in the art.

Further modification of the initial product of formula (I), by methods known in the art and illustrated in the Examples below, may be used to prepare additional compounds of this invention.

Starting materials of the formula II wherein n is 2 and Y is O, may be prepared by the method outlined in Scheme 3

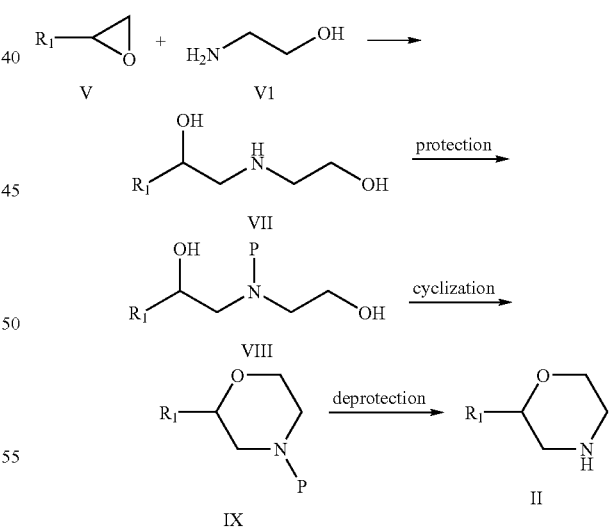

As outlined in Scheme 2, reacting a starting material of formula TI with an acid of formula Hal-Ar—COOH provides a coupled compound of formula IV. The appropriately substituted starting amine TI may be obtained either commercially or made by procedures known to one skilled in the art. Standard peptide coupling reactions known in the art (see for example M. Bodanszky, 1984, The Practice of Peptide Synthesis, Springer-Verlag) may be employed in these syntheses.

As illustrated in Scheme 3, reacting an epoxide of formula V with amino ethanol VI, provides a diol of formula VII. Reacting the compound of formula VII with di-t-butyl dicarbonate, in a suitable solvent such as methylene chloride, in the presence of a base such as triethylamine provides a N—protected compound of the formula VIII, wherein P is a protecting group such as BOC. Cyclizing compound VIII in a suitable solvent such as toluene, in the presence of triphenyl phosphine and diethylazodicarboxylate followed by deprotection under standard conditions, provides compound of formula II.

EXPERIMENTAL EXAMPLES

Example 1

(5-tert-Butyl-isoxazol-3-yl)-[5-((S)-2-phenyl-morpholin-4-ylmethyl)-pyridin-2-yl]-amine (S)-2-(2-Hydroxy-ethylamino)-1-phenyl-ethanol

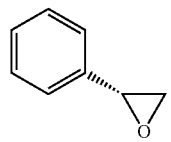 + 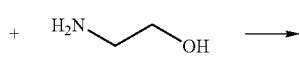

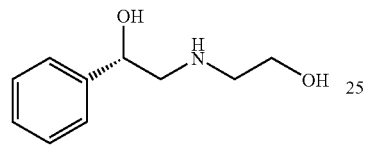

5 g of (S)-(+)-styrene oxide and 15.410 mL ethanol amine were stirred at room temperature overnight. The solution is poured into water and the water was extracted with dichloromethane. The combined dichloromethane layers were washed with brine and concentrated in vacuo. The oil was used crude. Assumed quantitative yield carried on to the next step. Theoretical wt: 7.9 g (S)-(2-Hydroxy-ethyl)-(2-hydroxy-2-phenyl-ethyl)-carbamic acid tert-butyl ester

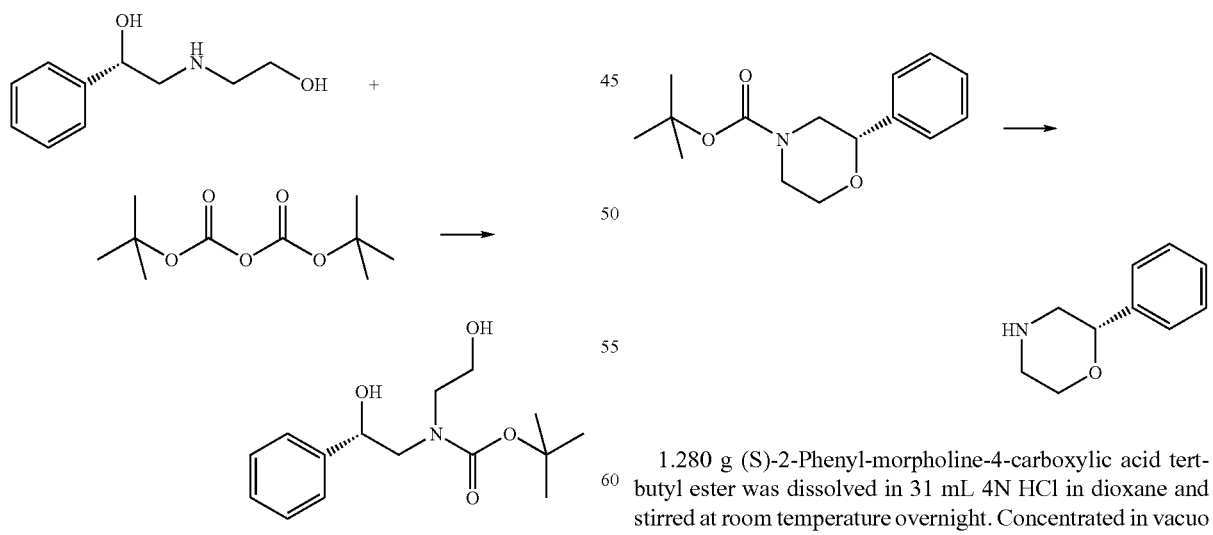

7.920 g (S)-2-(2-Hydroxy-ethylamino)-1-phenyl-ethanol and 10.5 g di-t-butyl dicarbonate in 262 mL methylene chloride were stirred together at room temperature and 9.14 mL triethylamine was added. The solution was stirred at room temperature overnight. The solution was then poured into water and extracted with methylene chloride. The combined organics were washed with brine and dried with sodium sulfate. After filtration, the crude material was purified by flash chromatography. Wt: 3.1832 g, 26% yield (S)-2-Phenyl-morpholine-4-carboxylic acid tert-butyl ester

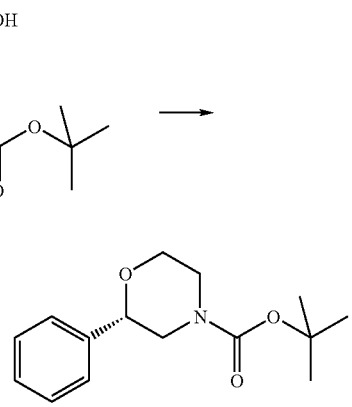

3 g of (S)-(2-Hydroxy-ethyl)-(2-hydroxy-2-phenyl-ethyl)-carbamic acid tert-butyl ester and 0.327 g of triphenylphosphine were dissolved in 53.3 mL toluene. 0.217 g of diethylazodicarboxylate in 5.4 mL toluene was added dropwise to the resulting solution at room temperature under argon atmosphere and the mixture was stirred overnight. The solvent was removed in vacuo and the material purified by column chromatography.

(S)-2-Phenyl-morpholine

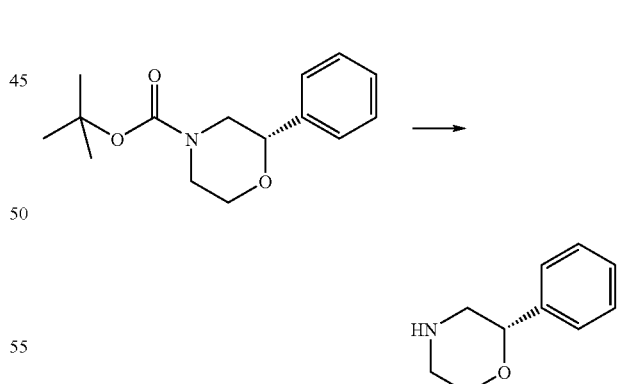

1.280 g (S)-2-Phenyl-morpholine-4-carboxylic acid tert-butyl ester was dissolved in 31 mL 4N HCl in dioxane and stirred at room temperature overnight. Concentrated in vacuo and diluted with 1N HCl. The aqueous was extracted with ether and then basicified to pH 12-14 with 2N NaOH followed by extraction with DCM. The organic layers were dried over Na2SO4, filtered and concentrated in vacuo to afford 617 mg of product by H NMR. 78% yield.

(S)-4-(6-Chloro-pyridin-3-ylmethyl)-2-phenyl-morpholine

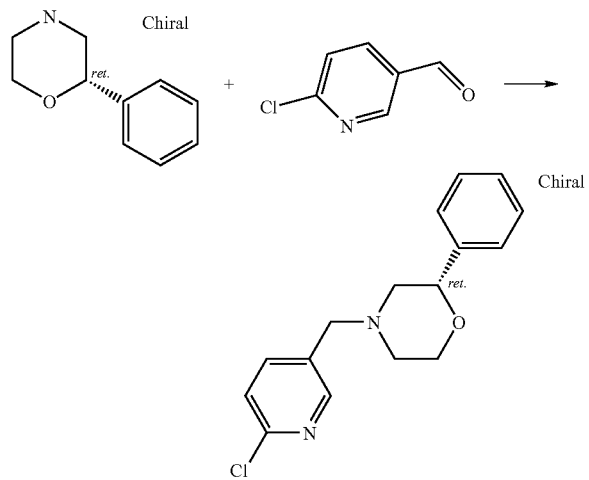

10 g of (S)-2-Phenyl-morpholine was dissolved in 610 mL of dichloroethane. 10.407 g of 6-Chloropyridine-3-carboxaldehyde was added and the reaction stirred at room temperature for 30 minutes followed by addition of 23.4 g of sodium triacetoxyborohydride. After stirring overnight at room temperature, the solution was poured into an aqueous saturated sodium bicarbonate solution and the layers separated. The organic layer was washed several times with aqueous saturated sodium bicarbonate solution followed by brine. It was then dried over sodium sulfate, filtered and concentrated in vacuo. Purification was accomplished by flash chromatography to afford 11.23 g of product. 63.5% yield. EI m/z 289=MH$^+$

(5-tert-Butyl-isoxazol-3-yl)-[5-((S)-2-phenyl-morpholin-4-ylmethyl)-pyridin-2-yl]-amine 2.73 mL of (S)-4-(6-Chloro-pyridin-3-ylmethyl)-2-phenyl-morpholine in DMSO(0.1M solution) was added to 63 mg of 5-tert-Butyl-isoxazol-3-ylamine. 900 L of sodium bis(trimethylsilyl)amide (1M solution in tetrahydrofuran) was added and the reaction heated overnight at 60° C. on an orbital shaker. The reaction was filtered through a fritted cartridge. Purification was accomplished by preparatory liquid chromatography to give the title compound in 24% yield. EI m/z 393=MH$^+$

Example 2

(4-Methoxy-phenyl)-[5-((S)-2-phenyl-morpholin-4-ylmethyl)-pyridin-2-yl]-amine

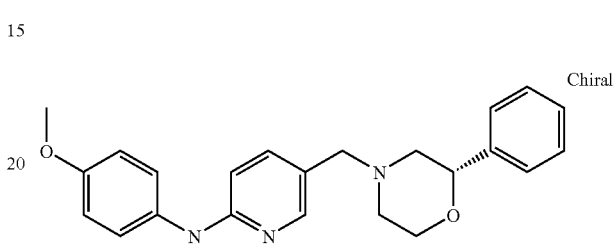

The above compound was made in a similar manner as Example 1 but with the appropriate aniline. 43.5% yield. EI m/z 376=MH$^+$

Example 3

(4-Ethoxy-phenyl)-[5-((S)-2-phenyl-morpholin-4-ylmethyl)-pyridin-2-yl]-amine

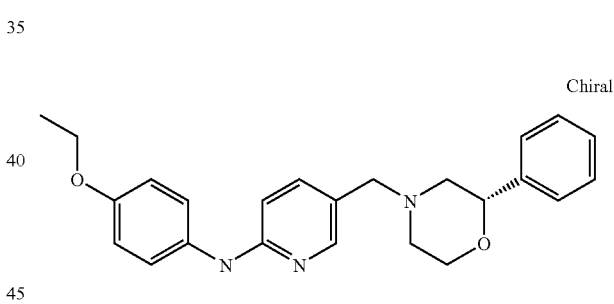

The above compound was made in a similar manner as Example 1 but with the appropriate aniline. 43% yield. EI m/z 390=MH$^+$

Example 4

[5-((S)-2-Phenyl-morpholin-4-ylmethyl)-pyridin-2-yl]-(4-trifluoromethoxy-phenyl)-amine

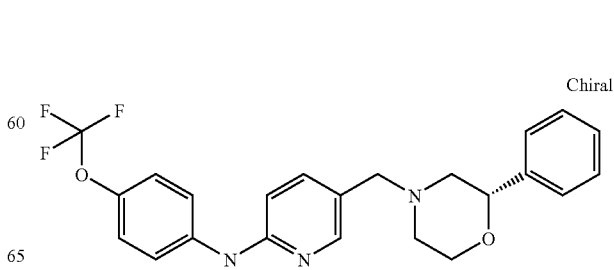

The above compound was made in a similar manner as Example 1 but with the appropriate aniline. 46% yield. EI m/z 430=MH⁺

Example 5

(4-Ethyl-phenyl)-[5-((S)-2-phenyl-morpholin-4-ylmethyl)-pyridin-2-yl]-amine

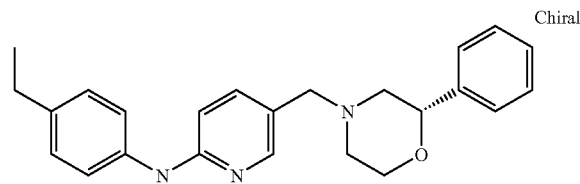

The above compound was made in a similar manner as Example 1 but with the appropriate aniline. 36% yield. EI m/z 374=MH⁺

Example 6

Naphthalen-1-yl-[5-((S)-2-phenyl-morpholin-4-ylmethyl)-pyridin-2-yl]-amine

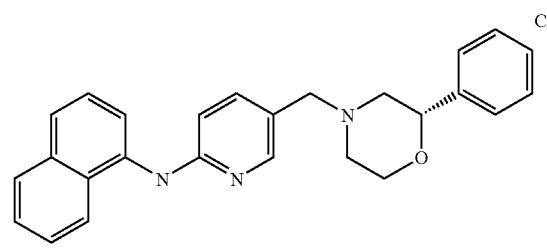

The above compound was made in a similar manner as Example 1 but with the appropriate aniline. 31% yield. EI m/z 396=MH⁺

Example 7

Naphthalen-2-yl-[5-((S)-2-phenyl-morpholin-4-ylmethyl)-pyridin-2-yl]-amine

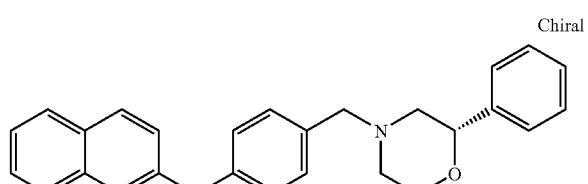

The above compound was made in a similar manner as Example 1 but with the appropriate aniline. 17% yield. EI m/z 396=MH⁺

Example 8

[5-((S)-2-Phenyl-morpholin-4-ylmethyl)-pyridin-2-yl]-pyrimidin-4-yl-amine

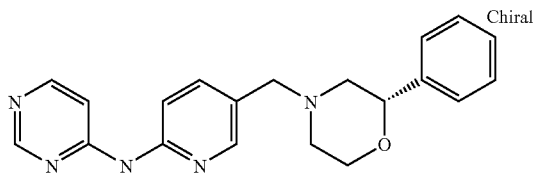

The above compound was made in a similar manner as Example 1 but with the appropriate aniline and heating was done in microwave reactor at 200° C. for 15 minutes. 22% yield. EI m/z 348=MH⁺

Example 9

[5-((S)-2-Phenyl-morpholin-4-ylmethyl)-pyridin-2-yl]-pyridin-3-yl-amine

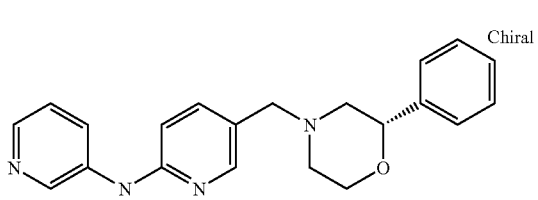

The above compound was made in a similar manner as Example 1 but with the appropriate aniline. 52% yield. EI m/z 347=MH⁺

Example 10

[5-((S)-2-Phenyl-morpholin-4-ylmethyl)-pyridin-2-yl]-pyridin-4-yl-amine

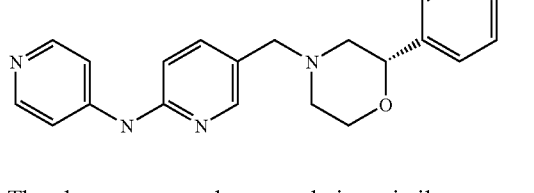

The above compound was made in a similar manner as Example 1 but with the appropriate aniline. 20% yield. EI m/z 347=MH⁺

Example 11

[5-((S)-2-Phenyl-morpholin-4-ylmethyl)-pyridin-2-yl]-quinolin-3-yl-amine

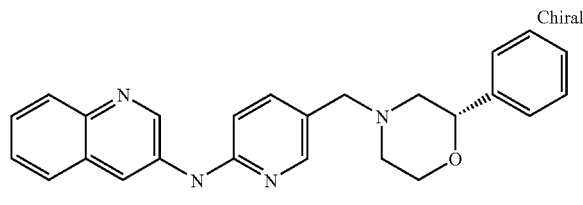

The above compound was made in a similar manner as Example 1 but with the appropriate aniline. 59% yield. EI m/z 397=MH+

Example 12

[5-((S)-2-Phenyl-morpholin-4-ylmethyl)-pyridin-2-yl]-quinolin-5-yl-amine

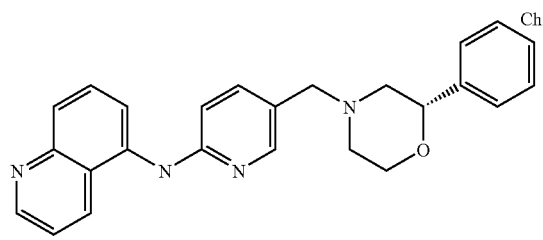

The above compound was made in a similar manner as Example 1 but with the appropriate aniline. 51% yield. EI m/z 397=MH+

Example 13

[5-((S)-2-Phenyl-morpholin-4-ylmethyl)-pyridin-2-yl]-quinolin-8-yl-amine

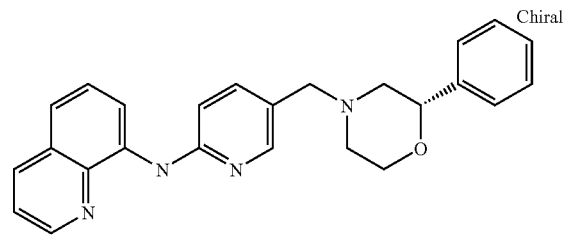

The above compound was made in a similar manner as Example 1 but with the appropriate aniline. 34% yield. EI m/z 397=MH+

Example 14

Isoquinolin-5-yl-[5-((S)-2-phenyl-morpholin-4-ylmethyl)-pyridin-2-yl]-amine

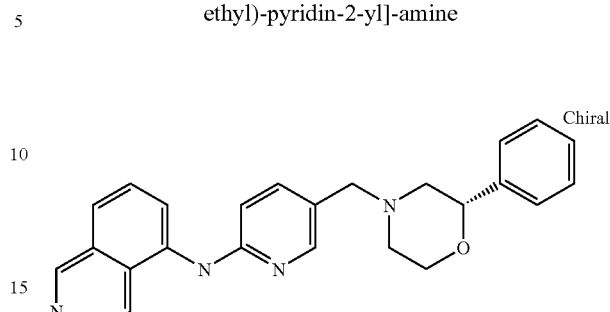

The above compound was made in a similar manner as Example 1 but with the appropriate aniline. 40% yield. EI m/z 397=MH+

Example 15

Phenyl-[5-((S)-2-phenyl-morpholin-4-ylmethyl)-pyridin-2-yl]-amine

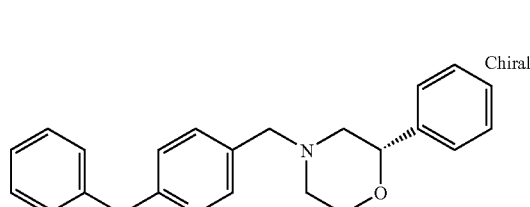

The above compound was made in a similar manner as Example 1 but with the appropriate aniline and heating was done in microwave reactor at 200° C. for 15 minutes. 31% yield. EI m/z 346=MH+

Example 16

(2-Fluoro-phenyl)-[5-((S)-2-phenyl-morpholin-4-ylmethyl)-pyridin-2-yl]-amine

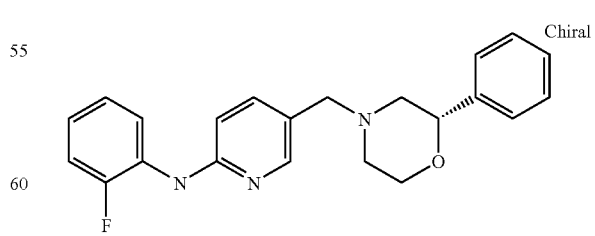

The above compound was made in a similar manner as Example 1 but with the appropriate aniline. 37% yield. EI m/z 364=MH+

Example 17

(2-Chloro-phenyl)-[5-((S)-2-phenyl-morpholin-4-ylmethyl)-pyridin-2-yl]-amine

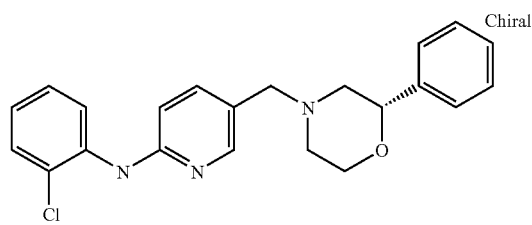

The above compound was made in a similar manner as Example 1 but with the appropriate aniline and heating was done in microwave reactor at 200° C. for 15 minutes. 34% yield. EI m/z 380=MH$^+$ Example 18

(2,3-Dichloro-phenyl)-[5-((S)-2-phenyl-morpholin-4-ylmethyl)-pyridin-2-yl]-amine

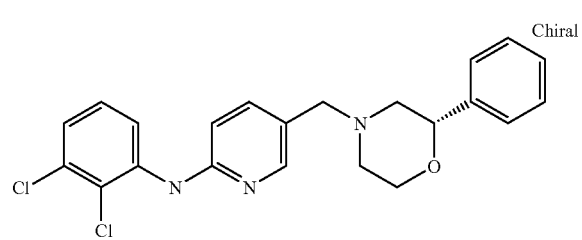

The above compound was made in a similar manner as Example 1 but with the appropriate aniline and heating was done in microwave reactor at 200° C. for 15 minutes. 32% yield. EI m/z 414=MH$^+$ Example 19

(2,4-Dichloro-phenyl)-[5-((S)-2-phenyl-morpholin-4-ylmethyl)-pyridin-2-yl]-amine

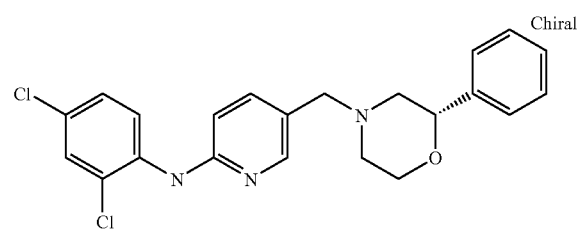

The above compound was made in a similar manner as Example 1 but with the appropriate aniline. 22% yield. EI m/z 414=MH$^+$ Example 20

(2,5-Dichloro-phenyl)-[5-((S)-2-phenyl-morpholin-4-ylmethyl)-pyridin-2-yl]-amine

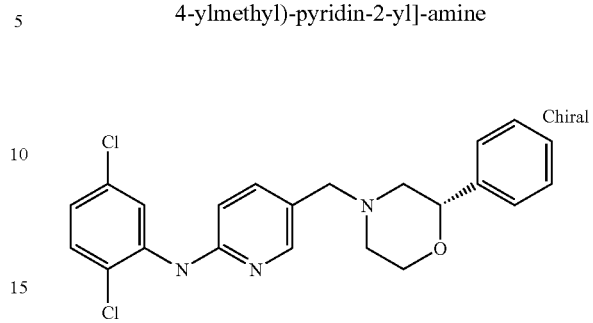

The above compound was made in a similar manner as Example 1 but with the appropriate aniline. 29% yield. EI m/z 414=MH$^+$ Example 21

(2-Methoxy-phenyl)-[5-((S)-2-phenyl-morpholin-4-ylmethyl)-pyridin-2-yl]-amine

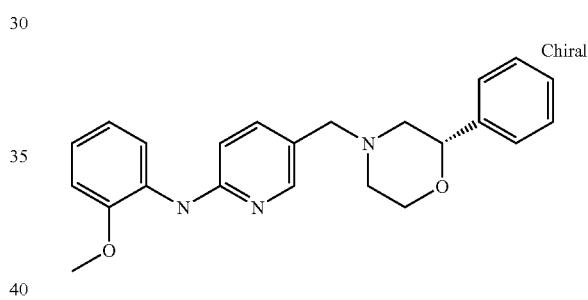

The above compound was made in a similar manner as Example 1 but with the appropriate aniline. 30% yield. EI m/z 376=MH$^+$ Example 22

(2-Ethoxy-phenyl)-[5-((S)-2-phenyl-morpholin-4-ylmethyl)-pyridin-2-yl]-amine

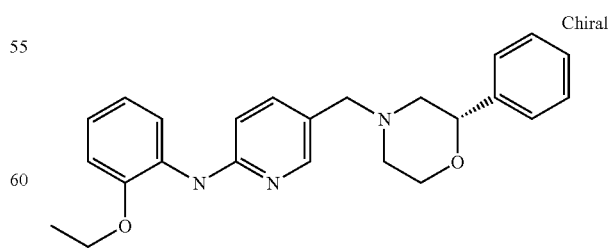

The above compound was made in a similar manner as Example 1 but with the appropriate aniline. 34% yield. EI m/z 390=MH$^+$

Example 23

(2-Isopropyl-phenyl)-[5-((S)-2-phenyl-morpholin-4-ylmethyl)-pyridin-2-yl]-amine

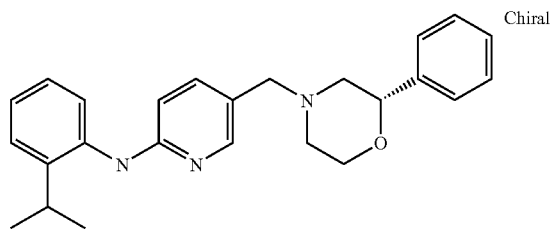

The above compound was made in a similar manner as Example 1 but with the appropriate aniline. 25% yield. EI m/z 388=MH+

Example 24

[5-((S)-2-Phenyl-morpholin-4-ylmethyl)-pyridin-2-yl]-o-tolyl-amine

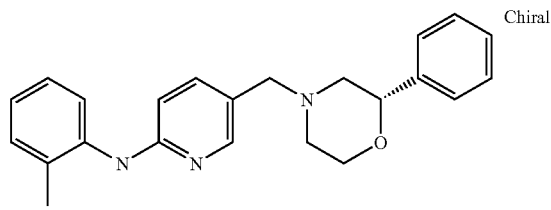

The above compound was made in a similar manner as Example 1 but with the appropriate aniline. 33% yield. EI m/z 360=MH+

Example 25

(3-Fluoro-phenyl)-[5-((S)-2-phenyl-morpholin-4-ylmethyl)-pyridin-2-yl]-amine

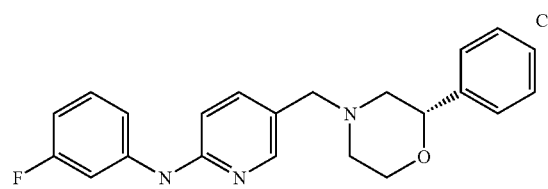

The above compound was made in a similar manner as Example 1 but with the appropriate aniline. 33% yield. EI m/z 364=MH+

Example 26

(3-Chloro-phenyl)-[5-((S)-2-phenyl-morpholin-4-ylmethyl)-pyridin-2-yl]-amine

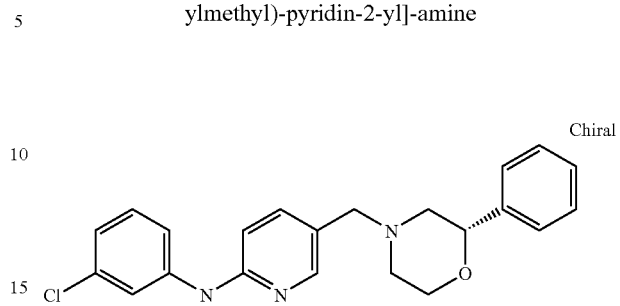

The above compound was made in a similar manner as Example 1 but with the appropriate aniline. 39% yield. EI m/z 380=MH+

Example 27

(3,4-Dichloro-phenyl)-[5-((S)-2-phenyl-morpholin-4-ylmethyl)-pyridin-2-yl]-amine

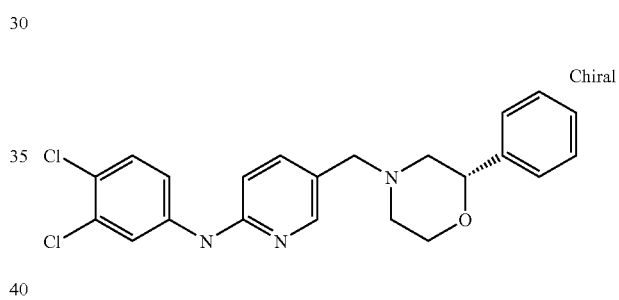

The above compound was made in a similar manner as Example 1 but with the appropriate aniline. 42% yield. EI m/z 414=MH+

Example 28

[5-((S)-2-Phenyl-morpholin-4-ylmethyl)-pyridin-2-yl]-m-tolyl-amine

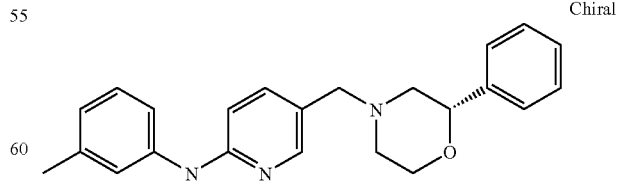

The above compound was made in a similar manner as Example 1 but with the appropriate aniline. 29% yield. EI m/z 360=MH+

Example 29

(4-Fluoro-phenyl)-[5-((S)-2-phenyl-morpholin-4-ylmethyl)-pyridin-2-yl]-amine

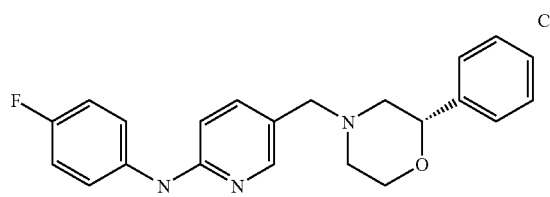

The above compound was made in a similar manner as Example 1 but with the appropriate aniline. 43% yield. EI m/z 364=MH$^+$

Example 30

(4-Chloro-phenyl)-[5-((S)-2-phenyl-morpholin-4-ylmethyl)-pyridin-2-yl]-amine

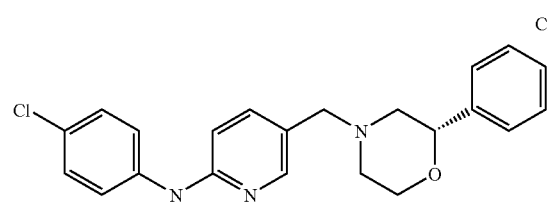

The above compound was made in a similar manner as Example 1 but with the appropriate aniline. 38% yield. EI m/z 380=MH$^+$

Example 31

[5-((S)-2-Phenyl-morpholin-4-ylmethyl)-pyridin-2-yl]-p-tolyl-amine

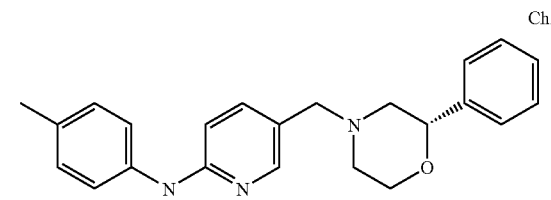

The above compound was made in a similar manner as Example 1 but with the appropriate aniline. 36% yield. EI m/z 360=MH$^+$

Example 32

[5-((S)-2-Phenyl-morpholin-4-ylmethyl)-pyridin-2-yl]-(2-trifluoromethoxy-phenyl)-amine

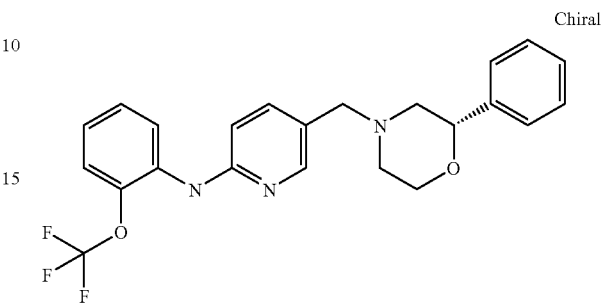

The above compound was made in a similar manner as Example 1 but with the appropriate aniline. 33% yield. EI m/z 430=MH$^+$

Example 33

Isoquinolin-3-yl-[5-((S)-2-phenyl-morpholin-4-ylmethyl)-pyridin-2-yl]-amine

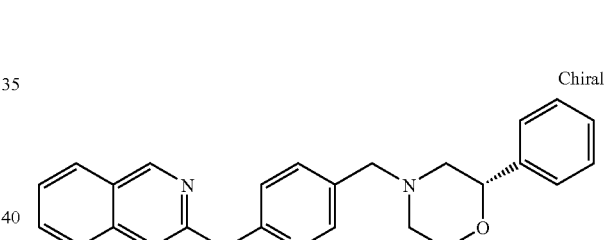

The above compound was made in a similar manner as Example 1 but with the appropriate aniline. 29% yield. EI m/z 397=MH$^+$

Example 34

(S)-4-(4-Phenoxy-benzyl)-2-phenyl-morpholine

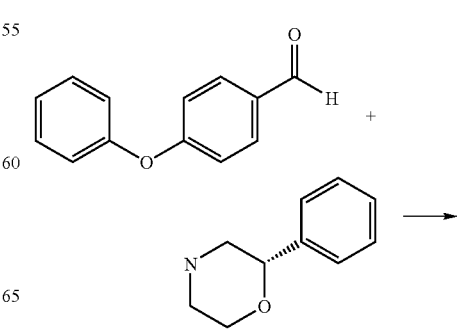

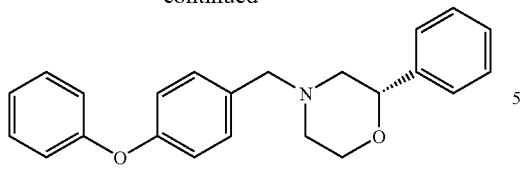

200 mg of (S)-2-Phenyl-morpholine (see synthesis in Example 1) was dissolved in 2 mL of dichloroethane and 253 μL of 4-Phenoxy-benzaldehyde was added. The reaction was stirred at room temperature 30 minutes and then 467 mg of sodium triacetoxyborohydride was added. The reaction was stirred overnight at room temperature. The reaction solution was then washed with aqueous saturated sodium bicarbonate solution several times followed by a brine wash. The organics were dried over sodium sulfate, filtered and concentrated in vacuo. Purification by preparatory chromatography gave the title compound. 8% yield. EI m/z 346=MH+

Example 35

(S)-4-(4-Benzenesulfonyl-benzyl)-2-phenyl-morpholine

4-Benzenesulfonyl-benzaldehyde

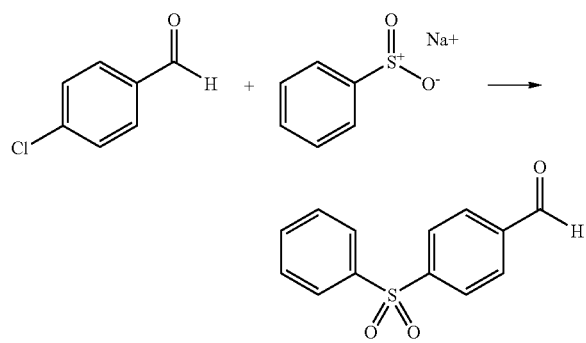

A microwave vessel was charged with 1 g of 4-chlorobenzaldehyde in 6 mL of DMSO and 1.75 g of sodium benzenesulfinate. The vessel was sealed and heated in a microwave reactor at 180° C. for 1.5 hours. The mixture was cooled and poured into 12 mL of ice water. Filtered and the solid was purified by flash chromatography using ethyl acetate/hexane as eluent mixtures to afford 1.34 g of the title compound. 76% yield.

(S)-4-(4-Benzenesulfonyl-benzyl)-2-phenyl-morpholine

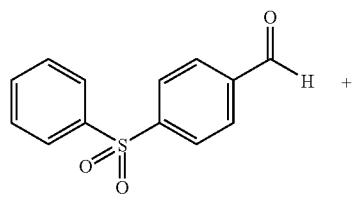

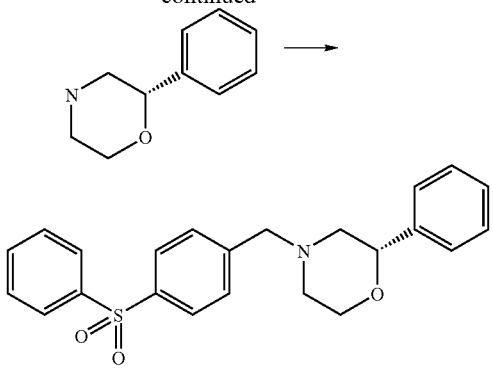

The above compound could be made in a similar manner as Example 34.

Assessment of Biological Properties

The biological properties of the compounds of the formula I were assessed using the assays described below.

A. Human CB1 and CB2 Receptor Binding:

Experimental Method:

CB2 membranes were purchased and made from HEK293 EBNA cells stably transfected with human CB2 receptor cDNA (Perkin Elmer Life and Analytical Sciences). CB1 membranes were isolated from HEK cells stably co-transfected with human CB1 receptor and Gα16 cDNA's. The membrane preparation was bound to scintillation beads (Ysi-Poly-L-lysine SPA beads, GE Healthcare) for 4 hours at room temperature in assay buffer containing 50 mM Tris, pH 7.5, 2.5 mM EDTA, 5 mM $MgCl_2$, 0.8% fatty acid free Bovine Serum Albumin. Unbound membrane was removed by washing in assay buffer. Membrane-bead mixture was added to 96-well assay plates in the amounts of 15 ug membrane per well (CB2) or 2.5 ug per well (CB1) and 1 mg SPA bead per well. Compounds were added to the membrane-bead mixture in dose-response concentrations ranging from $1 \times 10^{-5}$ M to $1 \times 10^{-10}$ M with 0.25% DMSO, final. The competition reaction was initiated with the addition of $^3$H-CP55940 (Perkin Elmer Life and Analytical Sciences) at a final concentration of 1.5 nM (CB2) or 2.5 nM (CB1). The reaction was incubated at room temperature for 18 hours and read on TopCount NXT plate reader. Total and non-specific binding was determined in the absence and presence of 1.25 uM Win 55212 (Sigma). $IC_{50}$ values for each compound were calculated as the concentration of compound that inhibits the specific binding of the radioactively labeled ligand to the receptor by 50% using the XLFit 4.1 four parameter logistic model. $IC_{50}$ values were converted to inhibition constant (Ki) values using Cheng-Prusoff equation.

B. CB2R Mediated Modulation of cAMP Synthesis:

Compounds of the invention were evaluated for their CB2 agonist or inverse agonist activity in accordance with the following experimental method. Compounds which were shown to bind to CB2 by the binding assay described above but which were not shown to exhibit CB2R-mediated modulation of cAMP synthesis by this assay were presumed to be CB2 antagonists.

Experimental Method:

CHO cells expressing human CB2R (Euroscreen) were plated at a density of 5000 cells per well in 384 well plates and incubated overnight at 37° C. After removing the media, the cells were treated with test compounds diluted in stimulation buffer containing 1 mM IBMX, 0.25% BSA and 10 uM Forskolin. The assay was incubated for 30 minutes at 37° C.

Cells were lysed and the cAMP concentration was measured using DiscoverX-XS cAMP kit, following the manufacturer's protocol. In this setting, agonists will decrease forskolin induced production of cAMP while inverse agonists will further increase forskolin induced production of cAMP. EC50 of agonists were calculated as follows. The maximal amount of cAMP produced by forskolin compared to the level of cAMP inhibited by 1 uM CP55940 is defined as 100%. The EC50 value of each test compound was determined as the concentration at which 50% of the forskolin-stimulated cAMP synthesis was inhibited. Data was analyzed using a four-parameter logistic model. (Model 205 of XLfit 4.0).

C. CB1R Mediated Modulation of cAMP Synthesis:

Compounds of the invention were evaluated for their CB1 agonist or inverse agonistic activity in accordance with the following experimental method. Compounds which were shown to bind to CB1 by the binding assay described above but which were not shown to exhibit CB1R-mediated modulation of cAMP synthesis by this assay were presumed to be CB1 antagonists.

Experimental Method:

CHO cells expressing human CB1R (Euroscreen) were plated at a density of 5000 cells per well in 384 well plates and incubated overnight at 37° C. After removing the media, the cells were treated with test compounds diluted in stimulation buffer containing 1 mM IBMX, 0.25% BSA and 10 uM Forskolin. The assay was incubated for 30 minutes at 37° C. Cells were lysed and the cAMP concentration was measured using DiscoverX-XS cAMP kit, following the manufacturer's protocol. In this setting, agonists will decrease forskolin induced production of cAMP while inverse agonists will further increase forskolin induced production of cAMP. EC50 of agonists were calculated as follows. The maximal amount of cAMP produced by forskolin compared to the level of cAMP inhibited by 1 uM CP55940 is defined as 100%. The EC50 value of each test compound was determined as the concentration at which 50% of the forskolin-stimulated cAMP synthesis was inhibited. Data was analyzed using a four-parameter logistic model. (Model 205 of XLfit 4.0).

Compounds Having Agonist Activity

Through the use of the above described assays the following compounds were found to exhibit activity:

(5-tert-Butyl-isoxazol-3-yl)-[5-((S)-2-phenyl-morpholin-4-ylmethyl)-pyridin-2-yl]-amine;
(4-Methoxy-phenyl)-[5-((S)-2-phenyl-morpholin-4-ylmethyl)-pyridin-2-yl]-amine;
(4-Ethoxy-phenyl)-[5-((S)-2-phenyl-morpholin-4-ylmethyl)-pyridin-2-yl]-amine;
[5-((S)-2-Phenyl-morpholin-4-ylmethyl)-pyridin-2-yl]-(4-trifluoromethoxy-phenyl)-amine;
(4-Ethyl-phenyl)-[5-((S)-2-phenyl-morpholin-4-ylmethyl)-pyridin-2-yl]-amine;
Naphthalen-1-yl-[5-((S)-2-phenyl-morpholin-4-ylmethyl)-pyridin-2-yl]-amine;
Naphthalen-2-yl-[5-((S)-2-phenyl-morpholin-4-ylmethyl)-pyridin-2-yl]-amine;
[5-((S)-2-Phenyl-morpholin-4-ylmethyl)-pyridin-2-yl]-pyrimidin-4-yl-amine;
[5-((S)-2-Phenyl-morpholin-4-ylmethyl)-pyridin-2-yl]-pyridin-3-yl-amine;
[5-((S)-2-Phenyl-morpholin-4-ylmethyl)-pyridin-2-yl]-pyridin-4-yl-amine;
[5-((S)-2-Phenyl-morpholin-4-ylmethyl)-pyridin-2-yl]-quinolin-3-yl-amine;
[5-((S)-2-Phenyl-morpholin-4-ylmethyl)-pyridin-2-yl]-quinolin-5-yl-amine;
[5-((S)-2-Phenyl-morpholin-4-ylmethyl)-pyridin-2-yl]-quinolin-8-yl-amine;
Isoquinolin-5-yl-[5-((S)-2-phenyl-morpholin-4-ylmethyl)-pyridin-2-yl]-amine;
Phenyl-[5-((S)-2-phenyl-morpholin-4-ylmethyl)-pyridin-2-yl]-amine;
(2-Fluoro-phenyl)-[5-((S)-2-phenyl-morpholin-4-ylmethyl)-pyridin-2-yl]-amine;
(2-Chloro-phenyl)-[5-((S)-2-phenyl-morpholin-4-ylmethyl)-pyridin-2-yl]-amine;
(2;3-Dichloro-phenyl)-[5-((S)-2-phenyl-morpholin-4-ylmethyl)-pyridin-2-yl]-amine;
(2;4-Dichloro-phenyl)-[5-((S)-2-phenyl-morpholin-4-ylmethyl)-pyridin-2-yl]-amine;
(2;5-Dichloro-phenyl)-[5-((S)-2-phenyl-morpholin-4-ylmethyl)-pyridin-2-yl]-amine;
(2-Methoxy-phenyl)-[5-((S)-2-phenyl-morpholin-4-ylmethyl)-pyridin-2-yl]-amine;
(2-Ethoxy-phenyl)-[5-((S)-2-phenyl-morpholin-4-ylmethyl)-pyridin-2-yl]-amine;
(2-Isopropyl-phenyl)-[5-((S)-2-phenyl-morpholin-4-ylmethyl)-pyridin-2-yl]-amine;
[5-((S)-2-Phenyl-morpholin-4-ylmethyl)-pyridin-2-yl]-o-tolyl-amine;
(3-Fluoro-phenyl)-[5-((S)-2-phenyl-morpholin-4-ylmethyl)-pyridin-2-yl]-amine;
(3-Chloro-phenyl)-[5-((S)-2-phenyl-morpholin-4-ylmethyl)-pyridin-2-yl]-amine;
(3;4-Dichloro-phenyl)-[5-((S)-2-phenyl-morpholin-4-ylmethyl)-pyridin-2-yl]-amine;
[5-((S)-2-Phenyl-morpholin-4-ylmethyl)-pyridin-2-yl]-m-tolyl-amine;
(4-Fluoro-phenyl)-[5-((S)-2-phenyl-morpholin-4-ylmethyl)-pyridin-2-yl]-amine;
(4-Chloro-phenyl)-[5-((S)-2-phenyl-morpholin-4-ylmethyl)-pyridin-2-yl]-amine;
[5-((S)-2-Phenyl-morpholin-4-ylmethyl)-pyridin-2-yl]-p-tolyl-amine;
[5-((S)-2-Phenyl-morpholin-4-ylmethyl)-pyridin-2-yl]-(2-trifluoromethoxy-phenyl)-amine;
Isoquinolin-3-yl-[5-((S)-2-phenyl-morpholin-4-ylmethyl)-pyridin-2-yl]-amine; and
(S)-4-(4-Phenoxy-benzyl)-2-phenyl-morpholine.

The following compounds were found to exhibit agonistic activity and thus to be particularly well suited for the treatment of pain as well as for the treatment of inflammation.

(5-tert-Butyl-isoxazol-3-yl)-[5-((S)-2-phenyl-morpholin-4-ylmethyl)-pyridin-2-yl]-amine;
(4-Methoxy-phenyl)-[5-((S)-2-phenyl-morpholin-4-ylmethyl)-pyridin-2-yl]-amine;
(4-Ethoxy-phenyl)-[5-((S)-2-phenyl-morpholin-4-ylmethyl)-pyridin-2-yl]-amine;
[5-((S)-2-Phenyl-morpholin-4-ylmethyl)-pyridin-2-yl]-(4-trifluoromethoxy-phenyl)-amine;
(4-Ethyl-phenyl)-[5-((S)-2-phenyl-morpholin-4-ylmethyl)-pyridin-2-yl]-amine;
Naphthalen-1-yl-[5-((S)-2-phenyl-morpholin-4-ylmethyl)-pyridin-2-yl]-amine;
Naphthalen-2-yl-[5-((S)-2-phenyl-morpholin-4-ylmethyl)-pyridin-2-yl]-amine;
[5-((S)-2-Phenyl-morpholin-4-ylmethyl)-pyridin-2-yl]-pyrimidin-4-yl-amine;
[5-((S)-2-Phenyl-morpholin-4-ylmethyl)-pyridin-2-yl]-pyridin-3-yl-amine;
[5-((S)-2-Phenyl-morpholin-4-ylmethyl)-pyridin-2-yl]-pyridin-4-yl-amine;

[5-((S)-2-Phenyl-morpholin-4-ylmethyl)-pyridin-2-yl]-quinolin-3-yl-amine;
[5-((S)-2-Phenyl-morpholin-4-ylmethyl)-pyridin-2-yl]-quinolin-5-yl-amine;
[5-((S)-2-Phenyl-morpholin-4-ylmethyl)-pyridin-2-yl]-quinolin-8-yl-amine;
Isoquinolin-5-yl-[5-((S)-2-phenyl-morpholin-4-ylmethyl)-pyridin-2-yl]-amine;
Phenyl-[5-((S)-2-phenyl-morpholin-4-ylmethyl)-pyridin-2-yl]-amine;
(2-Fluoro-phenyl)-[5-((S)-2-phenyl-morpholin-4-ylmethyl)-pyridin-2-yl]-amine;
(2-Chloro-phenyl)-[5-((S)-2-phenyl-morpholin-4-ylmethyl)-pyridin-2-yl]-amine;
(2,3-Dichloro-phenyl)-[5-((S)-2-phenyl-morpholin-4-ylmethyl)-pyridin-2-yl]-amine;
(2,4-Dichloro-phenyl)-[5-((S)-2-phenyl-morpholin-4-ylmethyl)-pyridin-2-yl]-amine;
(2,5-Dichloro-phenyl)-[5-((S)-2-phenyl-morpholin-4-ylmethyl)-pyridin-2-yl]-amine;
(2-Methoxy-phenyl)-[5-((S)-2-phenyl-morpholin-4-ylmethyl)-pyridin-2-yl]-amine;
(2-Ethoxy-phenyl)-[5-((S)-2-phenyl-morpholin-4-ylmethyl)-pyridin-2-yl]-amine;
(2-Isopropyl-phenyl)-[5-((S)-2-phenyl-morpholin-4-ylmethyl)-pyridin-2-yl]-amine;
[5-((S)-2-Phenyl-morpholin-4-ylmethyl)-pyridin-2-yl]-o-tolyl-amine;
(3-Fluoro-phenyl)-[5-((S)-2-phenyl-morpholin-4-ylmethyl)-pyridin-2-yl]-amine;
(3-Chloro-phenyl)-[5-((S)-2-phenyl-morpholin-4-ylmethyl)-pyridin-2-yl]-amine;
(3,4-Dichloro-phenyl)-[5-((S)-2-phenyl-morpholin-4-ylmethyl)-pyridin-2-yl]-amine;
[5-((S)-2-Phenyl-morpholin-4-ylmethyl)-pyridin-2-yl]-m-tolyl-amine;
(4-Fluoro-phenyl)-[5-((S)-2-phenyl-morpholin-4-ylmethyl)-pyridin-2-yl]-amine;
(4-Chloro-phenyl)-[5-((S)-2-phenyl-morpholin-4-ylmethyl)-pyridin-2-yl]-amine;
[5-((S)-2-Phenyl-morpholin-4-ylmethyl)-pyridin-2-yl]-p-tolyl-amine;
[5-((S)-2-Phenyl-morpholin-4-ylmethyl)-pyridin-2-yl]-(2-trifluoromethoxy-phenyl)-amine;
Isoquinolin-3-yl-[5-((S)-2-phenyl-morpholin-4-ylmethyl)-pyridin-2-yl]-amine; and
(S)-4-(4-Phenoxy-benzyl)-2-phenyl-morpholine.

Of the above compounds, the following are preferred:
(4-Methoxy-phenyl)-[5-((S)-2-phenyl-morpholin-4-ylmethyl)-pyridin-2-yl]-amine;
[5-((S)-2-Phenyl-morpholin-4-ylmethyl)-pyridin-2-yl]-(4-trifluoromethoxy-phenyl)-amine;
(4-Ethyl-phenyl)-[5-((S)-2-phenyl-morpholin-4-ylmethyl)-pyridin-2-yl]-amine;
Naphthalen-1-yl-[5-((S)-2-phenyl-morpholin-4-ylmethyl)-pyridin-2-yl]-amine;
[5-((S)-2-Phenyl-morpholin-4-ylmethyl)-pyridin-2-yl]-pyridin-3-yl-amine;
[5-((S)-2-Phenyl-morpholin-4-ylmethyl)-pyridin-2-yl]-quinolin-5-yl-amine;
Phenyl-[5-((S)-2-phenyl-morpholin-4-ylmethyl)-pyridin-2-yl]-amine;
(2-Fluoro-phenyl)-[5-((S)-2-phenyl-morpholin-4-ylmethyl)-pyridin-2-yl]-amine;
(2-Chloro-phenyl)-[5-((S)-2-phenyl-morpholin-4-ylmethyl)-pyridin-2-yl]-amine;
(2,4-Dichloro-phenyl)-[5-((S)-2-phenyl-morpholin-4-ylmethyl)-pyridin-2-yl]-amine;
(2,5-Dichloro-phenyl)-[5-((S)-2-phenyl-morpholin-4-ylmethyl)-pyridin-2-yl]-amine;
(2-Methoxy-phenyl)-[5-((S)-2-phenyl-morpholin-4-ylmethyl)-pyridin-2-yl]-amine;
(2-Ethoxy-phenyl)-[5-((S)-2-phenyl-morpholin-4-ylmethyl)-pyridin-2-yl]-amine;
(2-Isopropyl-phenyl)-[5-((S)-2-phenyl-morpholin-4-ylmethyl)-pyridin-2-yl]-amine;
[5-((S)-2-Phenyl-morpholin-4-ylmethyl)-pyridin-2-yl]-o-tolyl-amine;
(3-Fluoro-phenyl)-[5-((S)-2-phenyl-morpholin-4-ylmethyl)-pyridin-2-yl]-amine;
(3,4-Dichloro-phenyl)-[5-((S)-2-phenyl-morpholin-4-ylmethyl)-pyridin-2-yl]-amine;
(4-Fluoro-phenyl)-[5-((S)-2-phenyl-morpholin-4-ylmethyl)-pyridin-2-yl]-amine;
(4-Chloro-phenyl)-[5-((S)-2-phenyl-morpholin-4-ylmethyl)-pyridin-2-yl]-amine;
[5-((S)-2-Phenyl-morpholin-4-ylmethyl)-pyridin-2-yl]-p-tolyl-amine; and
[5-((S)-2-Phenyl-morpholin-4-ylmethyl)-pyridin-2-yl]-(2-trifluoromethoxy-phenyl)-amine Therapeutic Use As can be demonstrated by the assays described above, the compounds of the invention are useful in modulating the CB2 receptor function. By virtue of this fact, these compounds have therapeutic use in treating disease-states and conditions mediated by the CB2 receptor function or that would benefit from modulation of the CB2 receptor function. As the compounds of the invention modulate the CB2 receptor function, they have very useful anti-inflammatory and immune-suppressive activity and they can be used in patients as drugs, particularly in the form of pharmaceutical compositions as set forth below, for the treatment of disease-states and conditions.

The agonist, antagonist and inverse agonist compounds according to the invention can be used in patients as drugs for the treatment of the following disease-states or indications that are accompanied by inflammatory processes:

(i) Lung diseases: e.g. asthma, bronchitis, allergic rhinitis, emphysema, adult respiratory distress syndrome (ARDS), pigeon fancier's disease, farmer's lung, chronic obstructive pulmonary disease (COPD);

(ii) Rheumatic diseases or autoimmune diseases or musculoskeletal diseases: all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthroses); tendinitis, bursitis, osteoarthritis, traumatic arthritis; collagenoses of any genesis, e.g., systemic lupus erythematosus, scleroderma, polymyositis, dermatomyositis, Sjögren syndrome, Still disease, Felty syndrome; and osteoporosis and other bone resorption diseases;

(iii) Allergic diseases: all forms of allergic reactions, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis;

(iv) Vascular diseases: panarteritis nodosa, polyarteritis nodosa, periarteriris nodoa, arteritis temporalis, Wegner granulomatosis, giant cell arthritis, atherosclerosis, reperfusion injury and erythema nodosum;

(v) Dermatological diseases: e.g. dermatitis, psoriasis; sunburn, burns, eczema (vi) Renal diseases: e.g. nephrotic syndrome; and all types of nephritis, e.g., glomerulonephritis;
(vii) Hepatic diseases: e.g. acute liver cell disintegration; acute hepatitis of various genesis, e.g., viral, toxic, drug-induced; and chronically aggressive and/or chronically intermittent hepatitis;
(viii) Gastrointestinal diseases: e.g. inflammatory bowel diseases, irritable bowel syndrome, regional enteritis (Crohn disease), colitis ulcerosa; gastritis; aphthous ulcer, celiac disease, regional ileitis, gastro esophageal reflux disease
(ix) Neuroprotection: e.g. in the treatment of neurodegeneration following stroke; cardiac arrest; pulmonary bypass; traumatic brain injury; spinal cord injury or the like;
(x) Eye diseases: allergic keratitis, uveitis, or iritis; conjunctivitis; blepharitis; neuritis nervi optici; choroiditis; glaucoma and sympathetic ophthalmia;
(xi) Diseases of the ear, nose, and throat (ENT) area: e.g. tinnitus; allergic rhinitis or hay fever; otitis externa; caused by contact eczema, infection, etc.; and otitis media;
(xii) Neurological diseases: e.g. brain edema, particularly tumor-related brain edema; multiple sclerosis; acute encephalomyelitis; meningitis; acute spinal cord injury; trauma; dementia, particularly degenerative dementia (including senile dementia, Alzheimer's disease; Parkinson's disease and Creutzfeldt-Jacob disease; Huntington's chorea, Pick's disease; motor neuron disease), vascular dementia (including multi-infarct dementia) as well as dementia associated with intracranial space occupying lesions; infections and related conditions (including HIV infection); Guillain-Barre syndrome; myasthenia gravis, stroke; and various forms of seizures, e.g., nodding spasms;
(xiii) Blood diseases: acquired hemolytic anemia; aplastic anemia, and idiopathic thrombocytopenia;
(xiv) Tumor diseases: acute lymphatic leukemia; Hodgkin's disease, malignant lymphoma; lymphogranulomatoses; lymphosarcoma; solid malignant tumors; extensive metastases,
(xv) Endocrine diseases: endocrine opthalmopathy; endocrine orbitopathia; thyrotoxic crisis; Thyroiditis de Quervain; Hashimoto thyroiditis; Morbus Basedow; granulomatous thyroiditis; struma lymphomatosa; and Grave disease; type I diabetes (insulin-dependent diabetes)
(xvi) Organ and tissue transplantations and graft-versus-host diseases;
(xvii) Severe states of shock, e.g., septic shock, anaphylactic shock, and systemic inflammatory response syndrome (SIRS);
(xviii) Neuropathic pain: e.g. multiple sclerosis pain, diabetic neurapathy, non-herpetic neuralgia, trigeminal neuralgia, pain resulting from physical trauma, amputation, cancer, post-surgical pain,
(xix) Inflammatory and chronic pain, e.g., pain associated with rheumatoid arthritis, osteoarthritis, juvenile arthritis, spondylitis, gouty arthritis, psoriatric arthritis, muskoskeletal pain, fibromyalgia, lower back and neck pain, aprains and strains, sympathetically maintained pain, myositis, pain associated with migraine, dismenorrhea, headache, toothache, influenza and other viral infections such as the common cold, rheumatic fever, pain associated with functional bowel disease, such as non-ulcer dyspepsia, non-cardiac chest pain and irritable bowel syndrome, pain associated with myocardial ischemia,
(xx) various other disease-states or conditions including, restenosis following percutaneous transluminal coronary angioplasty, acute and chronic pain, atherosclerosis, reperfusion injury, congestive heart failure, myocardial infarction, thermal injury, multiple organ injury secondary to trauma, necrotizing enterocolitis and syndromes associated with hemodialysis, leukopheresis, and granulocyte transfusion, sarcoidosis, gingivitis, pyrexia.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy,* 20th Edition, A. Gennaro (ed.), Lippincott Williams & Wilkins, 2000; *Handbook of Pharmaceutical Additives,* Michael & Irene Ash (eds.), Gower, 1995; *Handbook of Pharmaceutical Excipients,* A. H. Kibbe (ed.), American Pharmaceutical As'n, 2000; and H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

Pharmaceutical compositions suitable for buccal (sub-lingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration comprise sterile aqueous preparations of a compound of the present invention. These preparations are preferably administered intravenously, although administration can also be effected by means of subcutaneous, intramuscular, or intradermal injection. Injectable pharmaceutical formulations are commonly based upon injectable sterile saline, phosphate-buffered saline, oleaginous suspensions, or other injectable carriers known in the art and are generally rendered sterile and isotonic with the blood. The injectable pharmaceutical formulations may therefore be provided as a sterile injectable solution or suspension in a nontoxic parenterally acceptable diluent or solvent, including 1,3-butanediol, water, Ringer's solution, isotonic sodium chloride solution, fixed oils such as synthetic mono- or diglycerides, fatty acids such as oleic acid, and the like. Such injectable pharmaceutical formulations are formulated according to the known art using suitable dispersing or setting agents and suspending agents. Injectable compositions will generally contain from 0.1 to 5% w/w of a compound of the invention.

Solid dosage forms for oral administration of the compounds include capsules, tablets, pills, powders, and granules. For such oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such solid pharmaceutical formulations may include formulations, as are well-known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds include emulsions, microemulsions, solutions, suspensions, syrups, and elixirs, optionally containing pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations. Furthermore, preferred compounds for the present invention can be administered in intranasal form via topical use of suitable intranasal vehicles. The formulations may also contain compatible conventional carriers, such as cream or ointment bases and ethanol or oleyl alcohol for lotions. Such carriers may be present as from about 1% up to about 98% of the formulation, more usually they will form up to about 80% of the formulation.

Transdermal administration is also possible. Pharmaceutical compositions suitable for transdermal administration can be presented as discrete patches adapted to remain in intimate contact with the epidermis of the recipient for a prolonged period of time. To be administered in the form of a transdermal delivery system, the dosage administration will, of course, be continuous rather than intermittent throughout the dosage regimen. Such patches suitably contain a compound of the invention in an optionally buffered, aqueous solution, dissolved and/or dispersed in an adhesive, or dispersed in a polymer. A suitable concentration of the active compound is about 1% to 35%, preferably about 3% to 15%.

For administration by inhalation, the compounds of the invention are conveniently delivered in the form of an aerosol spray from a pump spray device not requiring a propellant gas or from a pressurized pack or a nebulizer with the use of a suitable propellant, e.g., dichlorodifluoromethane, trichlorofluoromethane, dichlorotetrafluoroethane, tetrafluoroethane, heptafluoropropane, carbon dioxide, or other suitable gas. In any case, the aerosol spray dosage unit may be determined by providing a valve to deliver a metered amount so that the resulting metered dose inhaler (MDI) is used to administer the compounds of the invention in a reproducible and controlled way. Such inhaler, nebulizer, or atomizer devices are known in the prior art, for example, in PCT International Publication Nos. WO 97/12687 (particularly FIG. 6 thereof, which is the basis for the commercial RESPIMAT® nebulizer); WO 94/07607; WO 97/12683; and WO 97/20590, to which reference is hereby made and each of which is incorporated herein by reference in their entireties.

Rectal administration can be effected utilizing unit dose suppositories in which the compound is admixed with low-melting water-soluble or insoluble solids such as fats, cocoa butter, glycerinated gelatin, hydrogenated vegetable oils, mixtures of polyethylene glycols of various molecular weights, or fatty acid esters of polyethylene glycols, or the like. The active compound is usually a minor component, often from about 0.05 to 10% by weight, with the remainder being the base component.

In all of the above pharmaceutical compositions, the compounds of the invention are formulated with an acceptable carrier or excipient. The carriers or excipients used must, of course, be acceptable in the sense of being compatible with the other ingredients of the composition and must not be deleterious to the patient. The carrier or excipient can be a solid or a liquid, or both, and is preferably formulated with the compound of the invention as a unit-dose composition, for example, a tablet, which can contain from 0.05% to 95% by weight of the active compound. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyethylene glycol, waxes, and the like. Lubricants include sodium oleate, sodium stearate, magnesium stearate, sodium benzoate, sodium acetate, sodium chloride, and the like. Disintegrators include starch, methyl cellulose, agar, bentonite, xanthan gum, and the like.

Pharmaceutically acceptable carriers and excipients encompass all the foregoing additives and the like.

Examples of Pharmaceutical Formulations

A. TABLETS

| Component | Amount per tablet (mg) |
|---|---|
| active substance | 100 |
| lactose | 140 |
| corn starch | 240 |
| polyvinylpyrrolidone | 15 |
| magnesium stearate | 5 |
| TOTAL | 500 |

The finely ground active substance, lactose, and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B. TABLETS

| Component | Amount per tablet (mg) |
|---|---|
| active substance | 80 |
| lactose | 55 |
| corn starch | 190 |
| polyvinylpyrrolidone | 15 |
| magnesium stearate | 2 |
| microcrystalline cellulose | 35 |
| sodium-carboxymethyl starch | 23 |
| TOTAL | 400 |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

C. COATED TABLETS

| Component | Amount per tablet (mg) |
|---|---|
| active substance | 5 |
| lactose | 30 |
| corn starch | 41.5 |
| polyvinylpyrrolidone | 3 |
| magnesium stearate | 0.5 |
| TOTAL | 90 |

The active substance, corn starch, lactose, and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

D. CAPSULES

| Component | Amount per capsule (mg) |
|---|---|
| active substance | 50 |
| corn starch | 268.5 |
| magnesium stearate | 1.5 |
| TOTAL | 320 |

The substance and corn starch are mixed and moistened with water. The moist mass is screened and dried. The dry granules are screened and mixed with magnesium stearate. The finished mixture is packed into size 1 hard gelatine capsules.

E. AMPOULE SOLUTION

| Component | Amount per ampoule |
|---|---|
| active substance | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilized and sealed by fusion. The ampoules contain 5 mg, 25 mg, and 50 mg of active substance.

F. SUPPOSITORIES

| Component | Amount per suppository (mg) |
|---|---|
| active substance | 50 |
| solid fat | 1650 |
| TOTAL | 1700 |

The hard fat is melted. At 40° C., the ground active substance is homogeneously dispersed therein. The mixture is cooled to 38° C. and poured into slightly chilled suppository molds.

G. METERING AEROSOL

| Component | Amount |
|---|---|
| active substance | 0.005 |
| sorbitan trioleate | 0.1 |
| Monofluorotrichloromethane and difluorodichloromethane (2:3) | To 100 |

The suspension is transferred into a conventional aerosol container with a metering valve. Preferably, 50 μL of suspension are delivered per spray. The active substance may also be metered in higher doses if desired (e.g., 0.02% by weight).

| H. POWDER FOR INHALATION | |
| --- | --- |
| Component | Amount |
| active substance | 1.0 mg |
| lactose monohydrate | to 25 mg |

| I. POWDER FOR INHALATION | |
| --- | --- |
| Component | Amount |
| active substance | 2.0 mg |
| lactose monohydrate | to 25 mg |

| J. POWDER FOR INHALATION | |
| --- | --- |
| Component | Amount |
| active substance | 1.0 mg |
| lactose monohydrate | to 5 mg |

| K. POWDER FOR INHALATION | |
| --- | --- |
| Component | Amount |
| active substance | 2.0 mg |
| lactose monohydrate | to 5 mg |

In Examples H, I, J, and K, the powder for inhalation is produced in the usual way by mixing the individual ingredients together.

What is claimed is:

1. A compound of the formula

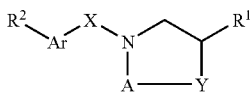

(I)

wherein,
$R^1$ is phenyl;
$R^2$ is $NR^5R^6$, $OR^6$, $SO_2R^6$, $CH_2R^6$ wherein $R^5$ is hydrogen or $C_1$-$C_6$ alkyl and $R^6$ is aryl or heteroaryl optionally substituted with 1-3 substituents selected from the group consisting of C1-6 alkyl chain, chlorine, fluorine, C1-3 alkoxy chain which is optionally substituted with fluorine, or a combination thereof or fused to an aromatic ring which is naphthyl or quinoline;
A is —$(CH_2)_2$—;
Y is O;
X is a methylene group (which is optionally mono- or disubstituted with methyl) or a carbonyl group; and,
Ar is a divalent moiety which is either phenylene or a 5-6 membered heteroarylene, which divalent moiety is optionally mono- or disubstituted with moieties selected from the group consisting of $C_1$-$C_6$ alkyl (optionally substituted by 1-3 halogens), $C_3$-$C_{10}$ cycloalkyl and halogen;

or the pharmaceutically acceptable salts thereof.

2. The compound according the claim 1 wherein,
$R^2$ is $NR^5R^6$, $OR^6$, $SO_2R^6$ or $CH_2R^6$, wherein $R^5$ is hydrogen and $R^6$ is a phenyl, quinolinyl, isoquinolinyl, pyridinyl, pyrimidinyl, or isoxazolyl which is optionally mono- or di-substituted with C1-6 alkyl chain, chlorine, fluorine, C1-3 alkoxy chain which is optionally substituted with fluorine, or a combination thereof or fused to an aromatic ring which is naphthyl or quinoline;
X is a methylene group; and,
Ar is a 1,4-phenylene or 1,4-pyridylene.

3. The compound according the claim 2 wherein,
$R^2$ is $NR^5R^6$, $OR^6$, $SO_2R^6$, $CH_2R^6$ wherein $R^5$ is hydrogen and $R^6$ is a phenyl, quinolinyl, isoquinolinyl, pyridinyl, or pyrimidinyl which is optionally mono- or di-substituted with C1-6 alkyl chain, chlorine, fluorine, C1-3 alkoxy chain which is optionally substituted with fluorine, or a combination thereof or fused to an aromatic ring which is naphthyl or quinoline; and,
Ar is a 1,4-phenylene or 1,4-pyridylene.

4. A pharmaceutical composition comprising a therapeutically effective amount of a compound according to claim 1.

5. A method of treating pain in an animal subject comprising administering to said animal subject in need of such treatment a therapeutically effective dose of the compound of claim 1.

6. A method of treating pain in an animal subject comprising administering to said animal subject in need of such treatment a therapeutically effective dose of the compound of claim 1, wherein the pain is selected from the group consisting of acute pain, visceral pain, neuropathic pain, inflammatory and nociceptive pain, and cancer pain.

7. A compound chosen from:
(5-tert-Butyl-isoxazol-3-yl)-[5-((S)-2-phenyl-morpholin-4-ylmethyl)-pyridin-2-yl]-amine;
(4-Methoxy-phenyl)-[5-((S)-2-phenyl-morpholin-4-ylmethyl)-pyridin-2-yl]-amine;
(4-Ethoxy-phenyl)-[5-((S)-2-phenyl-morpholin-4-ylmethyl)-pyridin-2-yl]-amine;
[5-((S)-2-Phenyl-morpholin-4-ylmethyl)-pyridin-2-yl]-(4-trifluoromethoxy-phenyl)-amine;
(4-Ethyl-phenyl)-[5-((S)-2-phenyl-morpholin-4-ylmethyl)-pyridin-2-yl]-amine;
Naphthalen-1-yl-[5-((S)-2-phenyl-morpholin-4-ylmethyl)-pyridin-2-yl]-amine;
Naphthalen-2-yl-[5-((S)-2-phenyl-morpholin-4-ylmethyl)-pyridin-2-yl]-amine;
[5-((S)-2-Phenyl-morpholin-4-ylmethyl)-pyridin-2-yl]-pyrimidin-4-yl-amine;
[5-((S)-2-Phenyl-morpholin-4-ylmethyl)-pyridin-2-yl]-pyridin-3-yl-amine;
[5-((S)-2-Phenyl-morpholin-4-ylmethyl)-pyridin-2-yl]-pyridin-4-yl-amine;
[5-((S)-2-Phenyl-morpholin-4-ylmethyl)-pyridin-2-yl]-quinolin-3-yl-amine;
[5-((S)-2-Phenyl-morpholin-4-ylmethyl)-pyridin-2-yl]-quinolin-5-yl-amine;
[5-((S)-2-Phenyl-morpholin-4-ylmethyl)-pyridin-2-yl]-quinolin-8-yl-amine;
Isoquinolin-5-yl-[5-((S)-2-phenyl-morpholin-4-ylmethyl)-pyridin-2-yl]-amine;
Phenyl-[5-((S)-2-phenyl-morpholin-4-ylmethyl)-pyridin-2-yl]-amine;
(2-Fluoro-phenyl)-[5-((S)-2-phenyl-morpholin-4-ylmethyl)-pyridin-2-yl]-amine;
(2-Chloro-phenyl)-[5-((S)-2-phenyl-morpholin-4-ylmethyl)-pyridin-2-yl]-amine;

(2,3-Dichloro-phenyl)-[5-((S)-2-phenyl-morpholin-4-yl-methyl)-pyridin-2-yl]-amine;
(2,4-Dichloro-phenyl)-[5-((S)-2-phenyl-morpholin-4-yl-methyl)-pyridin-2-yl]-amine;
(2,5-Dichloro-phenyl)-[5-((S)-2-phenyl-morpholin-4-yl-methyl)-pyridin-2-yl]-amine;
(2-Methoxy-phenyl)-[5-((S)-2-phenyl-morpholin-4-ylmethyl)-pyridin-2-yl]-amine;
(2-Ethoxy-phenyl)-[5-((S)-2-phenyl-morpholin-4-ylmethyl)-pyridin-2-yl]-amine;
(2-Isopropyl-phenyl)-[5-((S)-2-phenyl-morpholin-4-ylmethyl)-pyridin-2-yl]-amine;
[5-((S)-2-Phenyl-morpholin-4-ylmethyl)-pyridin-2-yl]-o-tolyl-amine;
(3-Fluoro-phenyl)-[5-((S)-2-phenyl-morpholin-4-ylmethyl)-pyridin-2-yl]-amine;
(3-Chloro-phenyl)-[5-((S)-2-phenyl-morpholin-4-ylmethyl)-pyridin-2-yl]-amine;
(3,4-Dichloro-phenyl)-[5-((S)-2-phenyl-morpholin-4-yl-methyl)-pyridin-2-yl]-amine;
[5-((S)-2-Phenyl-morpholin-4-ylmethyl)-pyridin-2-yl]-m-tolyl-amine;
(4-Fluoro-phenyl)-[5-((S)-2-phenyl-morpholin-4-ylmethyl)-pyridin-2-yl]-amine;
(4-Chloro-phenyl)-[5-((S)-2-phenyl-morpholin-4-ylmethyl)-pyridin-2-yl]-amine;
[5-((S)-2-Phenyl-morpholin-4-ylmethyl)-pyridin-2-yl]-p-tolyl-amine;
[5-((S)-2-Phenyl-morpholin-4-ylmethyl)-pyridin-2-yl]-(2-trifluoromethoxy-phenyl)-amine;
Isoquinolin-3-yl-[5-((S)-2-phenyl-morpholin-4-ylmethyl)-pyridin-2-yl]-amine; and
(S)-4-(4-Phenoxy-benzyl)-2-phenyl-morpholine;
or the pharmaceutically acceptable salts thereof.

* * * * *